United States Patent [19]

Olson

[11] Patent Number: 5,735,833
[45] Date of Patent: Apr. 7, 1998

[54] LAVAGE TIP

[75] Inventor: Daniel H. Olson, Louisville, Ohio

[73] Assignee: Bristol-Myers Squibb Co., New York, N.Y.

[21] Appl. No.: 762,684

[22] Filed: Dec. 11, 1996

[51] Int. Cl.$^6$ .............................. A61M 35/00; A61M 7/00
[52] U.S. Cl. ..................... 604/289; 604/290; 604/313; 604/35; 604/23
[58] Field of Search .................. 604/289, 290, 604/311, 312, 313, 35, 36, 23; 433/80, 96

[56] References Cited

U.S. PATENT DOCUMENTS

| | | | |
|---|---|---|---|
| Re. 28,405 | 5/1975 | Sollerud | 604/289 |
| D. 216,235 | 12/1969 | Slee et al. | D24/3 |
| D. 307,474 | 4/1990 | Cook | D24/25 |
| D. 344,133 | 2/1994 | Stamler | D24/130 |
| D. 345,016 | 3/1994 | Stamler | D24/130 |
| 517,274 | 3/1894 | Gollings | 604/289 |
| 1,178,898 | 4/1916 | Young . | |
| 2,612,892 | 10/1952 | Beatman | 604/313 |
| 2,812,765 | 11/1957 | Tofflemire | 128/276 |
| 2,957,577 | 3/1960 | Nicolaie | 604/313 |
| 3,208,145 | 9/1965 | Turner | 32/33 |
| 3,713,423 | 1/1973 | Sparr, Sr. | 604/289 |
| 4,294,251 | 10/1981 | Greenwald et al. | 128/276 |
| 4,299,221 | 11/1981 | Phillips et al. | 128/276 |
| 4,400,168 | 8/1983 | Buechel et al. | 604/48 |
| 4,487,600 | 12/1984 | Brownlie et al. | 604/35 |
| 4,692,140 | 9/1987 | Olson | 604/40 |
| 4,769,003 | 9/1988 | Stamler | 604/39 |
| 4,776,793 | 10/1988 | LaRocca | 433/96 |
| 4,798,599 | 1/1989 | Thomas | 604/290 |
| 4,807,625 | 2/1989 | Singleton | 128/361 |
| 4,865,545 | 9/1989 | LaRocca | 433/96 |
| 4,872,837 | 10/1989 | Issalene et al. | 433/29 |
| 4,898,588 | 2/1990 | Roberts | 604/187 |
| 5,037,437 | 8/1991 | Matsen, III | 623/16 |
| 5,133,701 | 7/1992 | Han | 604/289 |
| 5,224,940 | 7/1993 | Dann et al. | 604/290 |
| 5,520,667 | 5/1996 | Roche | 604/290 |
| 5,554,111 | 9/1996 | Morrey et al. | 604/26 |
| 5,558,646 | 9/1996 | Roche | 604/143 |

FOREIGN PATENT DOCUMENTS 0122467  11/1927  Switzerland .
0149564  12/1931  Switzerland .

OTHER PUBLICATIONS

Surgical Jet Lavage–Stryker Corporation–No date available.
SurgiLav Tips and Splash Shields–Stryker Corporation–Sep. 1976.
The Zimmer Var–A–Pulse Wound Debridgement System–Zimmer, Inc.–literature No. 97–5150–604–c1996.

*Primary Examiner*—John G. Weiss
*Assistant Examiner*—David J. Cho
*Attorney, Agent, or Firm*—Margaret L. Geringer

[57] ABSTRACT

The invention is directed to a lavage tip for use with a lavage system to irrigate living tissue. A fluid tip includes a fluid port and a suction or vacuum port, with the fluid port and vacuum port defining a cross-sectional area. A shield is connected to the fluid tip which has an open end with a surface area which is substantially larger than the cross-sectional area of the fluid tip. The open end of the shield is configured for placement against the tissue to be irrigated. The shield includes an articulating joint allowing relative angular movement between the shield and the fluid tip, whereby substantially all of the tissue to be irrigated at the open end of the shield may be irrigated without repositioning the open end relative to the tissue. The fluid tip may include an oxygen port for providing oxygen therapy to the tissue.

7 Claims, 2 Drawing Sheets

LAVAGE TIP

BACKGROUND OF THE INVENTION

1. Field of the Invention

The present invention relates to a lavage tip for use with a lavage system to irrigate living tissue, and, more particularly, to such a lavage tip including a shield or splash guard.

2. Description of the Related Art

Hand held lavage systems are used to irrigate living tissue, such as skin or bone, to facilitate the cleaning and irrigation of a wound or incision site. Typically, the irrigating liquid is expelled through a lavage tip toward the tissue. The lavage tip allows the irrigating fluid to be directed at a particular orientation to the tissue. The irrigating fluid which impinges upon the tissue usually results in a splash back of the fluid.

U.S. Pat. No. 4,692,140 (Olson) discloses a lavage/suction tip having a dual splash shield which surrounds a fluid tip. The dual splash shield arrangement includes an inner pliable or flexible shield and an outer substantially rigid shield which may selectively be positioned over the inner shield. The fluid tip ejects a particular pattern of spray onto the tissue to be irrigated at the open end of the splash shield. The surface area of the splash shield at the open end adjacent the tissue is only about 1.23 square inches.

SUMMARY OF THE INVENTION

The present invention provides a lavage tip having a shield which is attached via an articulating joint to a fluid tip. The articulating joint allows relative angular movement between the shield and the fluid tip such that the tissue to be irrigated at the open end of the shield may be irrigated without repositioning the open end relative to the tissue. An oxygen port may also be provided within the fluid tip to provide oxygen therapy to the tissue under the shield to promote faster healing. The lavage tip of the present invention is particularly beneficial for epidermal lavage, such as for external skin ulcers or other chronic wounds.

The invention comprises, in one form thereof, a lavage tip for use with a lavage system to irrigate living tissue. A fluid tip includes a fluid port and a suction or vacuum port, with the fluid port and vacuum port defining a cross-sectional area. A flexible and transparent shield is connected to the fluid tip. The shield has an open end with a surface area which is substantially larger than the cross-sectional area of the fluid tip. The open end of the shield is configured for placement against the tissue to be irrigated. The shield includes an articulating joint allowing relative angular movement between the shield and the fluid tip, whereby substantially all of the tissue to be irrigated at the open end of the shield may be irrigated without repositioning the open end relative to the tissue. The fluid tip may include an oxygen port for providing oxygen therapy to the tissue or wound site to promote faster healing.

An advantage of the present invention is that a relatively large area of tissue may be irrigated without repositioning the lavage tip relative to the tissue.

Another advantage is that oxygen therapy may be provided to the tissue simultaneously with liquid irrigation of the tissue.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
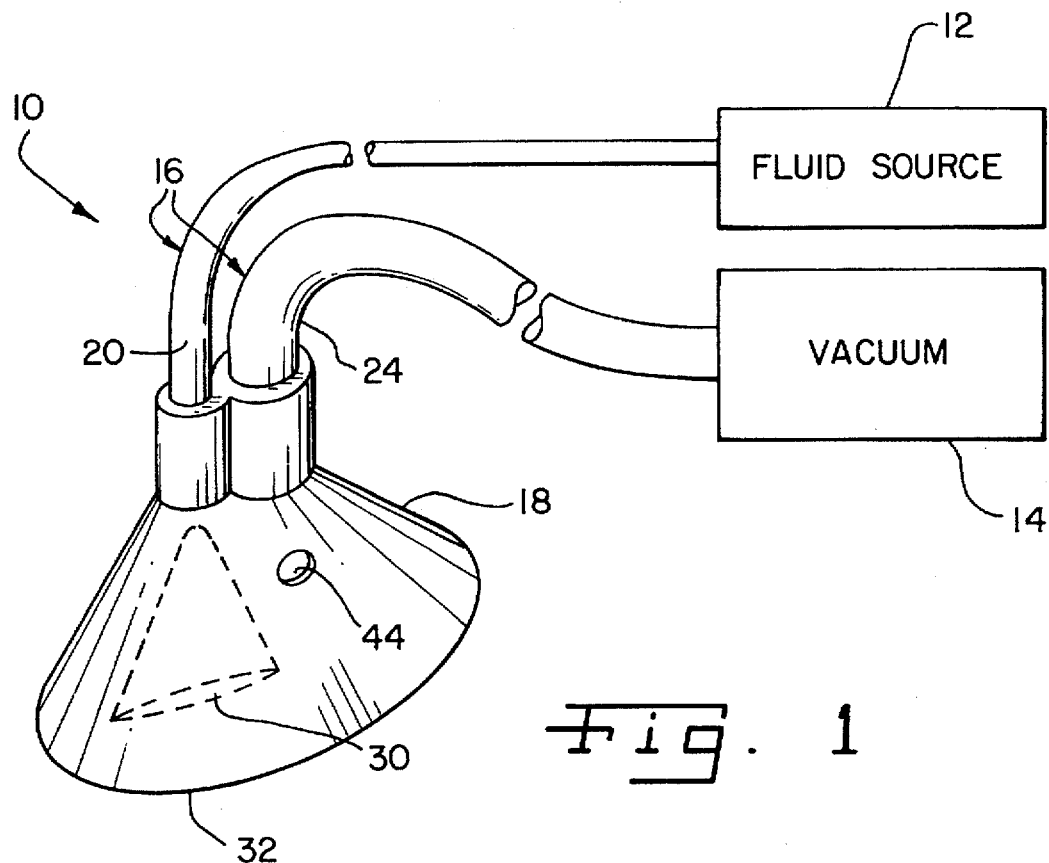
FIG. 1 is a perspective view of an embodiment of a lavage tip of the present invention.

Referring now to the drawings, and more particularly to FIGS. 1–4, there is shown an embodiment of a lavage tip 10 of the present invention. Lavage tip 10 may be used with a lavage system, including a fluid source 12 and a suction device 14, to irrigate living tissue, such as soft tissue at a wound or incision site, and is particularly suitable for irrigating epidermal tissue. Lavage tip 10 generally includes a fluid tip 16 and a shield 18.

Figure 2:
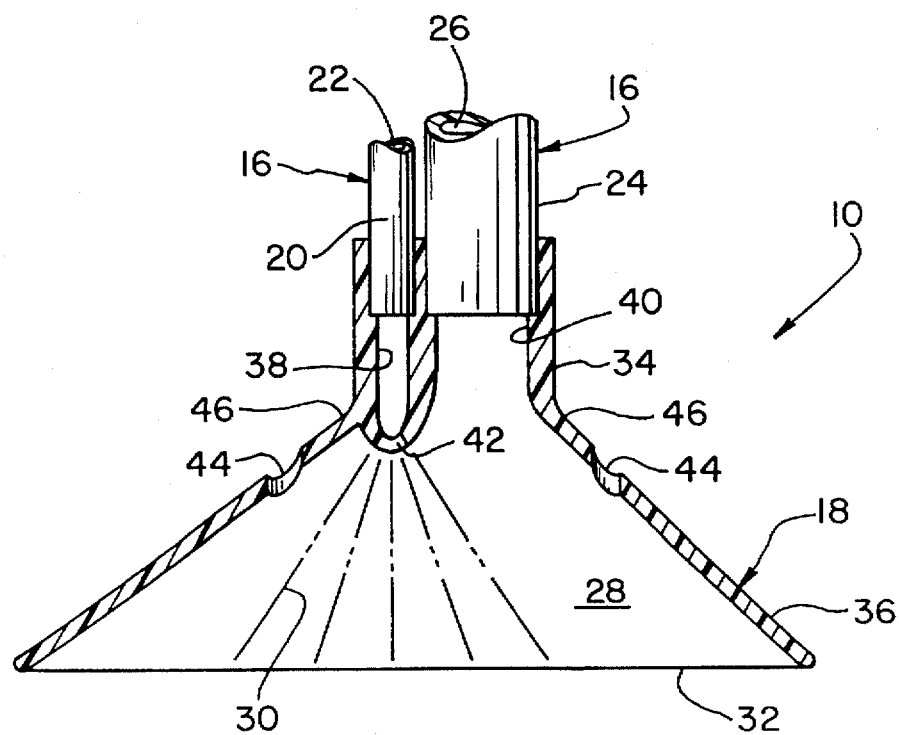
FIG. 2 is a side, partially sectioned view of the lavage tip shown in FIG. 1.

Fluid tip 16 includes a liquid delivery tube 20 defining a liquid port 22 (FIG. 2). Liquid delivery tube 20 is connected to a fluid source 12 which supplies an irrigating liquid to lavage tip 10. Liquid delivery tube 20 expels the irrigating liquid therefrom and into an internal chamber 28 of shield 18. In the particular embodiment shown, the expelled liquid impinges upon the tissue to be irrigated in a substantially fan-shaped pattern 30 (FIGS. 1 and 2).

Fluid tip 16 also includes a suction tube 24 defining a suction port 26. Suction tube 24 is connected to vacuum or suction device 14, and functions to remove irrigating liquid and debrided tissue from within shield 18 during operation of lavage tip 10.

In the particular embodiment shown in FIGS. 1–4, fluid tip 16 includes a liquid delivery tube 20 and a suction tube 24 which are separate from each other and individually attached to shield 18. However, it is also to be understood that liquid delivery tube 20 and suction tube 24 may be formed as an integral unit. Regardless of whether liquid delivery tube 20 and suction tube 24 are formed separately or as an integral unit, they conjunctively define a cross-sectional area which generally corresponds to the surface area which is required to attach fluid tip 16 to shield 18.

Shield 18 is a flexible and transparent shield having an open end 32 disposed generally opposite from fluid tip 16. Open end 32 defines a surface area (not numbered) which is substantially larger than the cross-sectional area of fan-shaped pattern 30 which is expelled from liquid delivery tube 20. In the embodiment shown in FIGS. 1–4, open end 32 has a surface area of between approximately 5 and 20 square inches, and preferably has a surface area of approximately 11 square inches.

Shield 18 includes a neck 34 formed monolithically therewith. Neck 34 interconnects fluid tip 16 with a generally frustroconical-shaped portion 36 of shield 18. More particularly, neck 34 includes a pair of openings 38, 40 in which liquid delivery tube 20 and suction tube 24 are received, respectively. Opening 38 also defines an orifice 42 which effects the fan-shaped pattern 30 of liquid irrigant. However, it will also be appreciated that the end of liquid delivery tube 20 may be formed so as to effect any suitable shaped pattern of liquid irrigant. A plurality of vacuum break holes 44 in frustroconical-shaped portion 36 of shield 18 may be selectively covered with the fingers of the user, and allow varying vacuum pressures to be created within internal chamber 28 by varying the amount of ambient air which enters chamber 28, as is known in the art. Internal chamber 28 is thus disposed in fluid communication with each of liquid port 22 and vacuum or suction port 26.

At the juncture between neck 34 and frustroconical-shaped portion 36 is an articulating joint 46 which allows relative angular movement between shield 18 and fluid tip 16. Such relative angular movement in turn allows the fan-shaped pattern 30 of liquid irrigant to be directed at different portions of the tissue under open end 32, without repositioning lavage tip 10 relative to the tissue to be irrigated. That is, by rotating or moving tip 16 relative to shield 18, substantially all of the tissue to be irrigated at open end 32 of shield 18 may be irrigated without repositioning open end 32 relative to the tissue. This results in faster operation since lavage tip 10 need not be repositioned as frequently relative to the tissue. Moreover, maintaining lavage system 10 in a single position or fewer positions relative to the tissue while at the same time irrigating all of the tissue under open end 32 reduces the amount of liquid which is not returned to vacuum device 14 via suction tube 24 since the seal or closure between shield 18 and the tissue is maintained over a larger surface area of the open end of shield 18.

Figure 3:
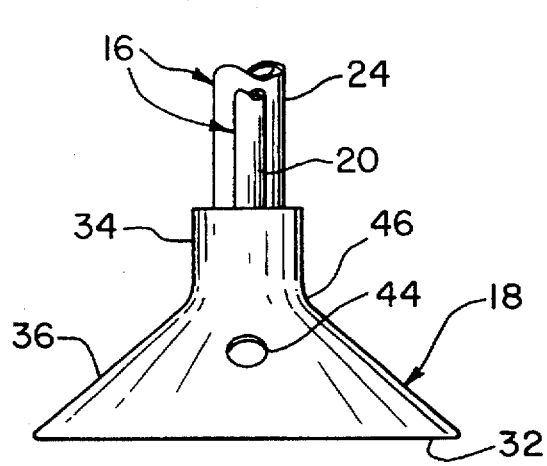
FIG. 3 is a side view of the lavage tip shown in FIGS. 1 and 2, with the fluid tip disposed in a particular angular orientation relative to the shield.
Figure 4:
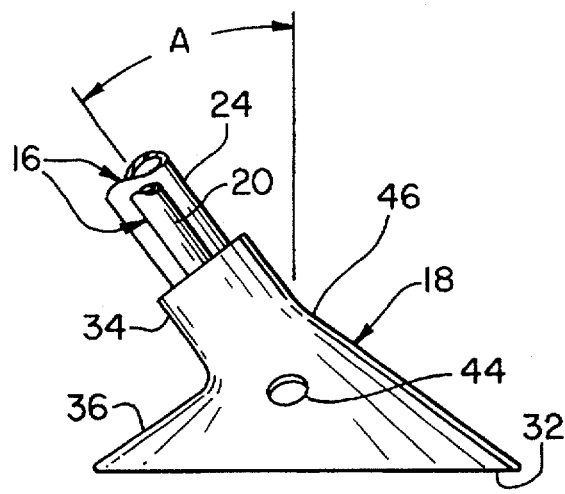
FIG. 4 is a side view of the lavage tip shown in FIGS. 1-3, with the fluid tip disposed in another angular orientation relative to the shield.

FIGS. 3 and 4 show side views of lavage tip 10 with shield 18 in two different positions relative to fluid tip 16. In FIG. 3, fluid tip 16 is disposed at a normal orientation, i.e., lacking external forces applied to lavage tip 10 by a user. In FIG. 4, fluid tip 16 and neck 34 are rotated relative to frustroconical-shaped portion 36 of shield 18. As is apparent, the majority of the elastic deformation in shield 18 occurs at articulating joint 46 between neck 34 and frustroconical-shaped portion 36. Even though fluid tip 16 is rotated relative to frustroconical-shaped portion 36, open end 32 still maintains the same approximate orientation as shown in FIG. 3. The articulating joint allows relative angular movement between the shield and the fluid tip between the normal position of FIG. 3 and the angulated position of FIG. 4. The angulated position may be angled up to about 45 to 90 degrees relative to the normal position, designated by angle A in FIG. 4.

Figure 5:
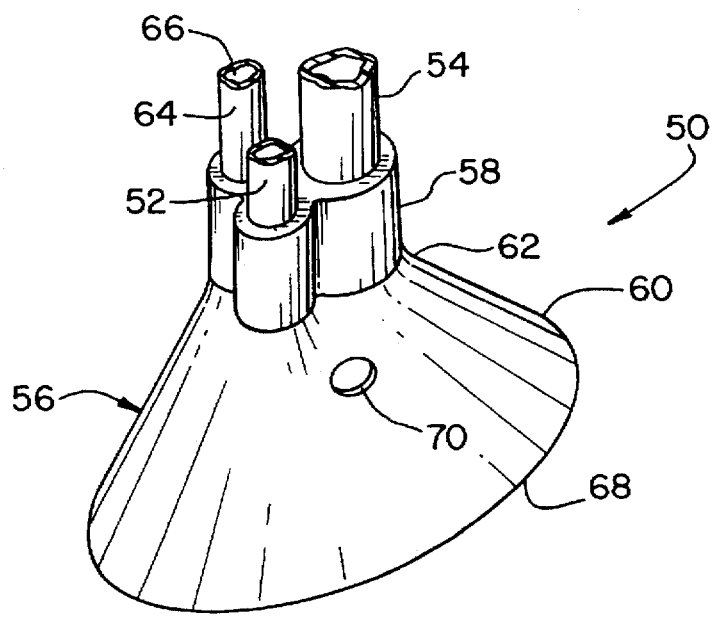
FIG. 5 is a perspective view of another embodiment of a lavage tip of the present invention, including an oxygen port.

FIG. 5 is a perspective view of another embodiment of a lavage tip 50 of the present invention. Lavage tip 50 is similar to lavage tip 10 shown in FIGS. 1–4 in that a liquid delivery tube 52 and a suction tube 54 are connected to a shield 56. Shield 56 includes a neck 58 connected to a frustroconical-shaped portion 60 via an articulating joint 62. However, lavage tip 50 differs from lavage tip 10 shown in FIGS. 1–4 in that an additional oxygen delivery tube 64 defining an oxygen point 66 is also connected to neck 58. Oxygen tube 64 is connected to a source of oxygen, $O_2$, (not shown) and allows oxygen to be expelled into an interior of shield 56 to provide oxygen therapy to the tissue under open end 68 of shield 56. Oxygen within shield 56 may be suctioned through suction tube 54 or at least partially escape to the ambient environment through vacuum break holes 70 (one of which is shown in FIG. 5). The oxygen therapy helps promote faster healing for epidermal lavage.

It is understood that this lavage tip 10 or 50 could be provided in various sizes, and the flexible shield 18 or 56 could be cut to the appropriate size as desired. Any suitable manufacturing methods may be used. In addition, the shield may be made out of 65 Durometer clear P.V.C., although any suitable materials may be utilized.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A lavage tip for use with an epidermal lavage system to irrigate living tissue, said lavage tip comprising:

a fluid tip including a fluid port, a suction port and an oxygen port; and a shield connected to said fluid tip, said shield having an open end configured for placement against the tissue to be irrigated, and wherein said shield defines an enlarged internal chamber which is disposed in fluid communication with each of said fluid port, said suction port and said oxygen port, and wherein said fluid port is configured for transporting an irrigating fluid to the chamber, said oxygen port is configured for transporting oxygen to the chamber to provide oxygen therapy to the tissue to promote faster healing, and said suction port is configured for transporting fluid from the chamber.

2. The lavage tip of claim 1, wherein said fluid port is configured for expelling the liquid onto the tissue in a particular spray pattern, and wherein said open end of said shield has a surface area which is substantially larger than said spray pattern, said open end being configured for placement against the tissue to be irrigated, said shield including an articulating joint allowing relative angular movement between said shield and said fluid tip, whereby substantially all of the tissue to be irrigated at said open end of said shield may be irrigated without repositioning said open end relative to the tissue.

3. The lavage tip of claim 2, wherein said surface area of said open end of said shield is between approximately 5 and 20 square inches.

4. The lavage tip of claim 3, wherein said surface area of said open end of said shield is approximately 11 square inches.

5. The lavage tip of claim 10, further comprising a neck attached to said shield and interconnecting said fluid tip with said shield, said articulating joint being disposed at a juncture between said neck and said shield.

6. The lavage tip of claim 2, wherein the articulating joint allows said relative angular movement between a normal, first position and a second angulated position which is angled up to about 45 to 90 degrees relative to the first position.

7. A method of providing epidermal lavage for irrigation of external skin conditions comprising the steps of:

a) providing a lavage tip comprising a fluid port, a suction port, and an oxygen port;

b) providing a shield connected to said fluid tip, said shield having an open end configured for placement against a skin surface, and wherein said shield defines an enlarged internal chamber which is disposed in fluid communication with each of said fluid port, said suction port, and said oxygen port;

c) applying fluid to said skin surface through said chamber; and d) applying oxygen to said skin surface under said enlarged chamber of said shield to help promote faster healing of said external skin condition; and e) providing suction to transport fluid from the chamber.

* * * * *